US007775662B2

(12) United States Patent
Kubota et al.

(10) Patent No.: US 7,775,662 B2
(45) Date of Patent: Aug. 17, 2010

(54) VISUAL ACUITY TESTING APPARATUS (75) Inventors: Atsushi Kubota, Tokyo (JP); Tomohiro Sakurada, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 232 days.

(21) Appl. No.: 11/984,959

(22) Filed: Nov. 26, 2007

(65) Prior Publication Data

US 2008/0158509 A1    Jul. 3, 2008

(30) Foreign Application Priority Data

Nov. 27, 2006   (JP)   ............................. 2006-318108

(51) Int. Cl.
*A61B 3/10* (2006.01)
(52) U.S. Cl. ..................................... 351/211
(58) Field of Classification Search ................. 359/211, 359/222, 227, 241, 243, 245, 246, 200, 205, 359/237, 238, 239
See application file for complete search history.

(56) References Cited

U.S. PATENT DOCUMENTS 5,822,446 A   10/1998   Kato 6,048,064 A * 4/2000 Hosoi et al. .................. 351/212
2006/0050238 A1   3/2006 Nakamura et al.

FOREIGN PATENT DOCUMENTS

JP        2002-143092        5/2002

* cited by examiner

*Primary Examiner*—Timothy J Thompson
*Assistant Examiner*—Tuyen Q Tra
(74) *Attorney, Agent, or Firm*—Dickstein Shapiro LLP (57) ABSTRACT A visual acuity testing apparatus includes a target presenting unit for displaying various targets to be presented to a subject's eye, an optical element arranging device for retaining various optical elements, and selectively arranging the optical element corresponding to a response from the subject between the subject's eye and the target presenting unit, an operation section which is operated for selecting each of targets and each of the optical elements, a display section for displaying an operation image illustrating an operation content of the operation section, a memory for storing a plurality of target data illustrating each of the targets and operation image data illustrating the operation image, an arithmetic control section for extracting the target data and the operation image data from the memory according to an operation of the operation section, and an image output section having at least two output ports.

9 Claims, 5 Drawing Sheets

VISUAL ACUITY TESTING APPARATUS

PRIORITY CLAIM

The present application is based on and claims priority from Japanese Application Number 2006-318108, filed on Nov. 27, 2006, the disclosure of which is hereby incorporated by reference herein its entirety.

BACKGROUND OF THE INVENTION

1. Field of the Invention

The present invention relates to a visual acuity testing apparatus for examining visual performance of a subject's eyes according to subjective determination of a subject.

2. Description of the Related Art

There is disclosed in JP2002-143092A, for example, a visual acuity testing apparatus for examining visual performance of a subject's eyes according to the response of a subject, so as to determine the refractivity of eyeglass lenses when making eyeglasses.

Such a visual acuity testing apparatus includes a target presenting unit for presenting various targets to the subject's eye, an optical element arrangement device, and a controller for controlling the operation of the target presenting unit and the optical element arrangement device. The optical element arrangement device includes a plurality of corrective lenses of optical elements for correcting the visual performance of the subject's eye, and selectively disposes between the subject's eye and the target presenting unit a corrective lens having refractive power according to the response from the subject. With this visual acuity testing apparatus, plural types of examinations can be conducted, and each of the examinations can be performed by using a target set for each of the examinations.

The controller includes an operation section which is operated for selecting the target to be presented to the subject's eye and the corrective lens, a display section for displaying the operation contents of the operation section, and a memory in which target data showing each of the targets and operation image data showing an operation image to be displayed onto the display section are stored. The controller also includes an arithmetic control section for extracting the target data corresponding to the target selected by the operation of the operation section and the operation image data from the memory, and an output section for outputting to the display section image signals indicating the operation image corresponding to the operation image data extracted by the arithmetic control section. The arithmetic control section sends driving control signals for displaying the target corresponding to the extracted target data to the target presenting unit.

The target presenting unit includes a memory, a plurality of target plates, a control section, and an arrangement device. The target data identical to the target data stored in the memory of the controller is stored in the memory. Each of the target plates includes targets corresponding to the target data stored in the memory. The control section extracts from the memory the target data of the driving control signals from the arithmetic control section of the controller. The arrangement device is driven for selectively arranging in front of the subject's eye the target plate corresponding to the target data extracted by the control section.

When examining the visual performance of a subject's eyes, at first, an examiner selects a target having a type corresponding to an examination type by the operation of the controller. The arrangement device is driven by the driving control signal received from the arithmetic control section of the controller, and the target plate corresponding to the target indicated by the driving control signal is thereby disposed in front of the subject's eyes. Next the examiner asks the subject about the visibility of the target when the subject looks at the target of the target plate via the corrective lens, and switches the corrective lens to a corrective lens corresponding to the vision ability of the subject's eye according to the response from the subject. The visual performance of the subject's eye is thereby corrected, and the value of the refractive power of the eyeglasses is determined.

However, since the target presenting unit for presenting each of the targets to the subject includes the memory in which the target data identical to the target data stored in the memory of the controller is stored and a plurality of target plates onto which the targets corresponding to the targets stored in the memory are marked, for example, when adding new target data into the memory of the controller, or changing the existing target data to the new target data, it is necessary to newly add into the memory of the target presenting unit the target data identical to the target data newly added into the memory of the controller and to newly add into the target presenting unit the target plate onto which the targets corresponding to the added target data are marked, or to change the target data of the memory of the target presenting unit to the target data identical to the target data of the memory of the controller and to change the target plate to a new target plate, in order to match the target types presentable in the target presenting unit with the target types selectable by the controller. For this reason, the operation for incorporating a new target into the visual acuity testing apparatus becomes complicated.

SUMMARY OF THE INVENTION

For the foregoing reasons, there is a need for a visual acuity testing apparatus capable of incorporating a new target easily.

A first aspect of the present invention relates to a visual acuity testing apparatus, including a target presenting unit for displaying various targets to be presented to a subject's eye, an optical element arranging device for retaining various optical elements, and selectively arranging the optical element corresponding to the response from the subject between the subject's eye and the target presenting unit, an operation section which is operated for selecting each of targets and each of the optical elements, a display section for displaying an operation image illustrating an operation content of the operation section, a memory for storing a plurality of target data illustrating each of the targets and operation image data illustrating the operation image, an arithmetic control section for extracting the target data and the operation image data from the memory according to an operation of the operation section, and an image output section having at least two output ports, wherein the image output section outputs to the display section via one output port an operation image signal corresponding to the operation image data extracted by the arithmetic control section, and outputs to at least one of the display section, the target presenting unit and an image display device via the other output port a target image signal corresponding to the target data extracted by the arithmetic control section.

Preferably, the image output section outputs the target image signal to the display section via the other output port, the target selected by the operation of the operation section is displayed on the display section together with the operation image, or the target selected by the operation of the operation section is displayed on the display section to be switchable with the operation image.

Preferably, the image output section outputs the target image signal to the display section via the other output port, the target selected by the operation of the operation section is displayed on the display section together with the operation image, and the target selected by the operation of the operation section is displayed on the display section to be switchable with the operation image.

Preferably, the image output section outputs the target image signal to the display section via the other output port, the display section includes a liquid crystal panel having liquid crystal capable of providing images different from each other from at least two directions, the target selected by the operation of the operation section is displayed on the display section so as to be visible from one direction, and the operation image is displayed on the display section to be visible from the other direction.

Preferably, the image output section outputs the target image signal to the image display device via the other output port.

Preferably, the memory stores a plurality of examination data illustrating contents of various examinations to be selected by the operation of the operation section, the arithmetic control section extracts the examination data corresponding to the examination selected by the operation of the operation section from the memory, and outputs a signal displaying the extracted examination data to the image output section, and the image output section outputs to the image display device an examination image signal for displaying onto the image display device an image displaying the contents of the examination according to a signal from the arithmetic control section.

DETAILED DESCRIPTION OF THE PREFERRED EMBODIMENTS

An embodiment of the present invention will be described with reference to the drawings.

Figure 1:
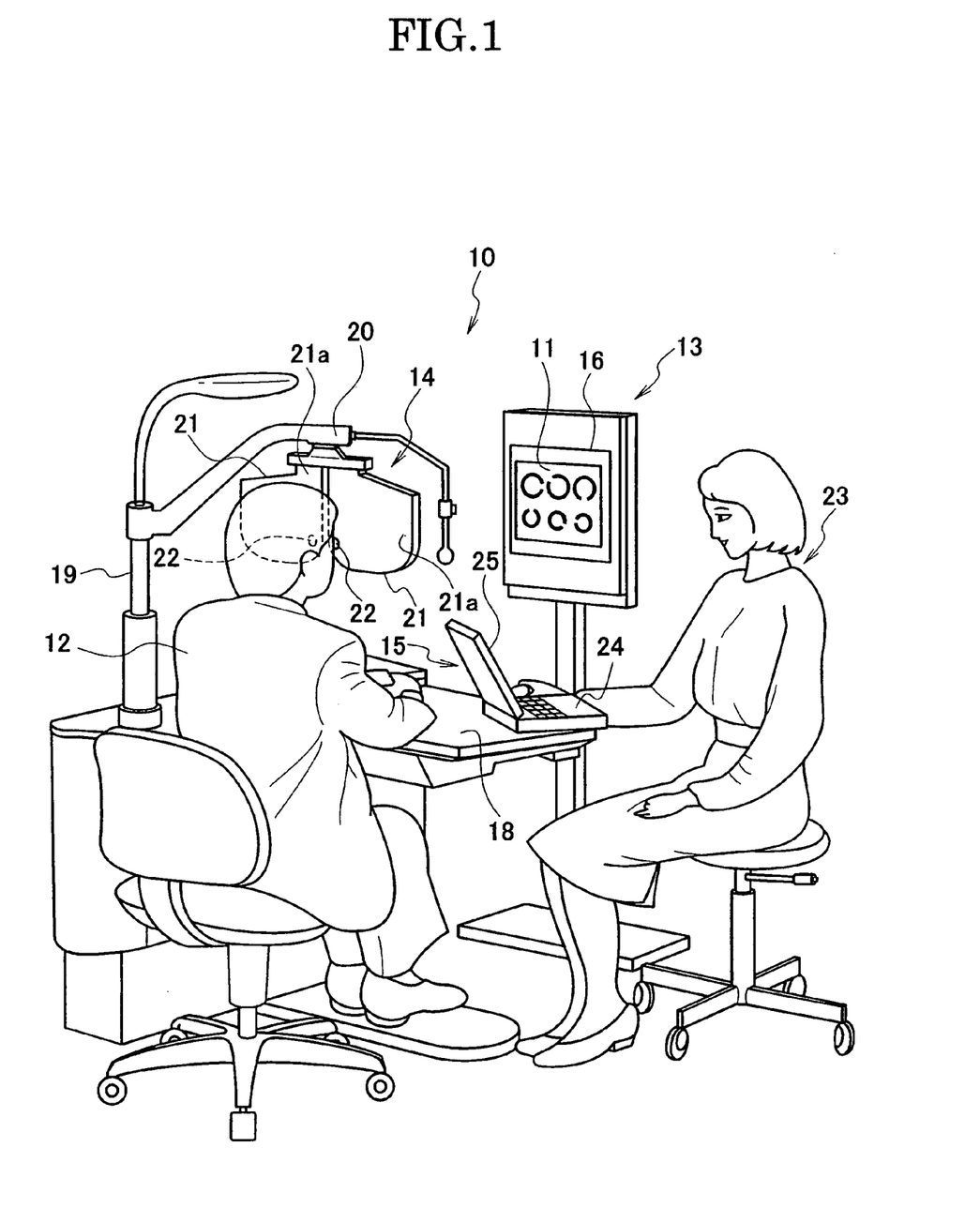
FIG. 1 is a perspective view illustrating a visual acuity testing apparatus according to one embodiment of the present invention.

Referring to FIG. 1, a subject optometer 10 according to the embodiment of the present invention includes a target presenting unit 13 for displaying various targets 11 to be presented to a subject's eye, and a corrective device 14 for correcting visual performance of the subject's eye. As is well known, the visual acuity testing apparatus 10 is used for determining refractivity of an eyeglass lens when making eyeglasses (not shown).

The target presenting unit 13 includes a display screen 16 onto which the targets 11 are displayed. In the example illustrated in FIG. 1, the display screen 16 is constituted of a liquid crystal panel. The targets 11 displayed on the display screen 16 are selected by control of an after-mentioned controller 15.

An optometry table 18 is disposed on a subject 12 side of the target presenting unit 13. The optometry table 18 includes a supporting post 19 extending upwardly from the table. The supporting post 19 has in the top part thereof an arm 20 extending in the lateral direction. The corrective device 14 is attached to the arm 20.

The corrective device 14 includes a pair of phoroptors 21 arranged in the right and left directions. Each of the phoroptors 21 includes a housing 21a having an optometry window 22. As is conventionally done, each of the housings 21a houses inside thereof a circular lens disk (not shown) in which a plurality of corrective lenses each having different refractive power is circumferentially-disposed. More particularly, the corrective device 14 constitutes an optical element arrangement device for selectively arranging the corrective lens of the optical element between the subject's eye and the target presenting unit 13. Each of the corrective lenses is selectively arranged in each of the optometry windows 22 by the rotation of the lens disk under the control of the controller 15.

The visual acuity testing apparatus 10 according to the embodiment of the present invention also includes a controller 15 for controlling the operation of the corrective device 14 and the target presenting unit 13.

Figure 2:
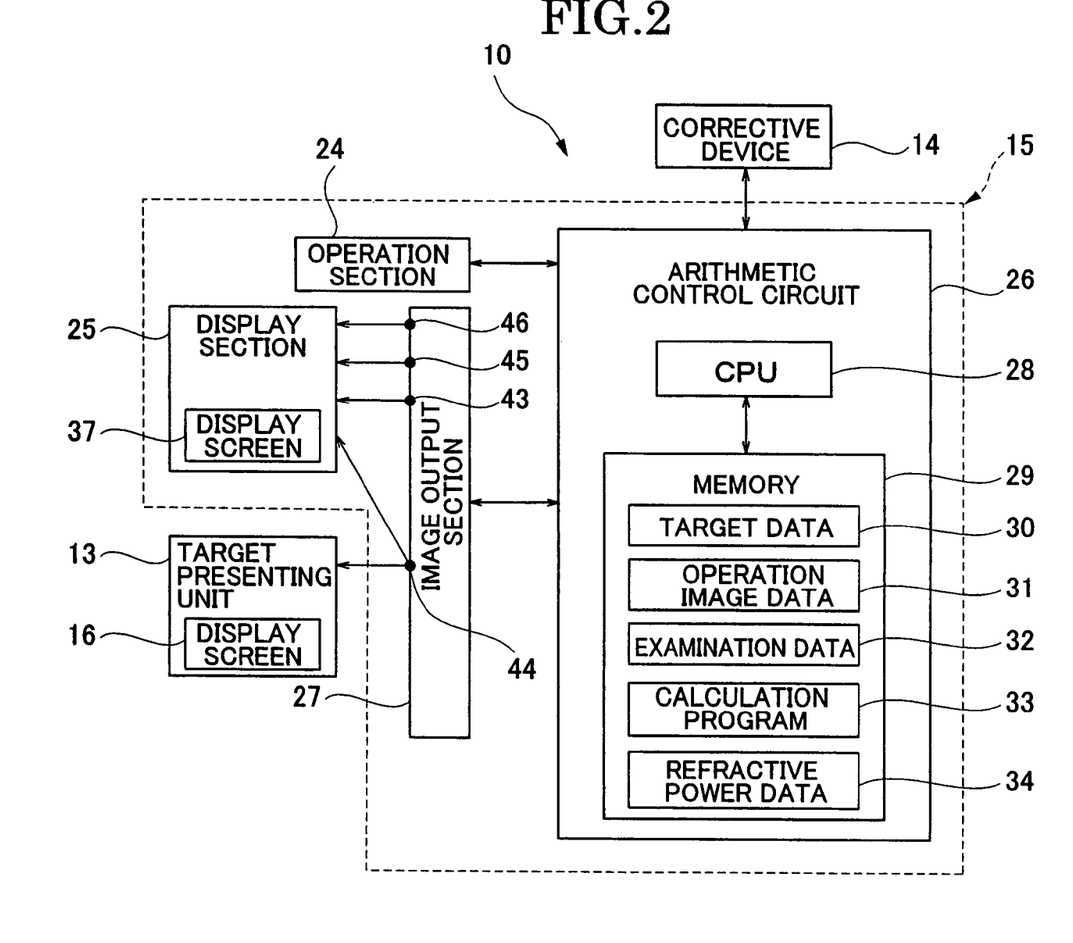
FIG. 2 is a block diagram illustrating the visual acuity testing apparatus according to one embodiment of the present invention.
Figure 3:
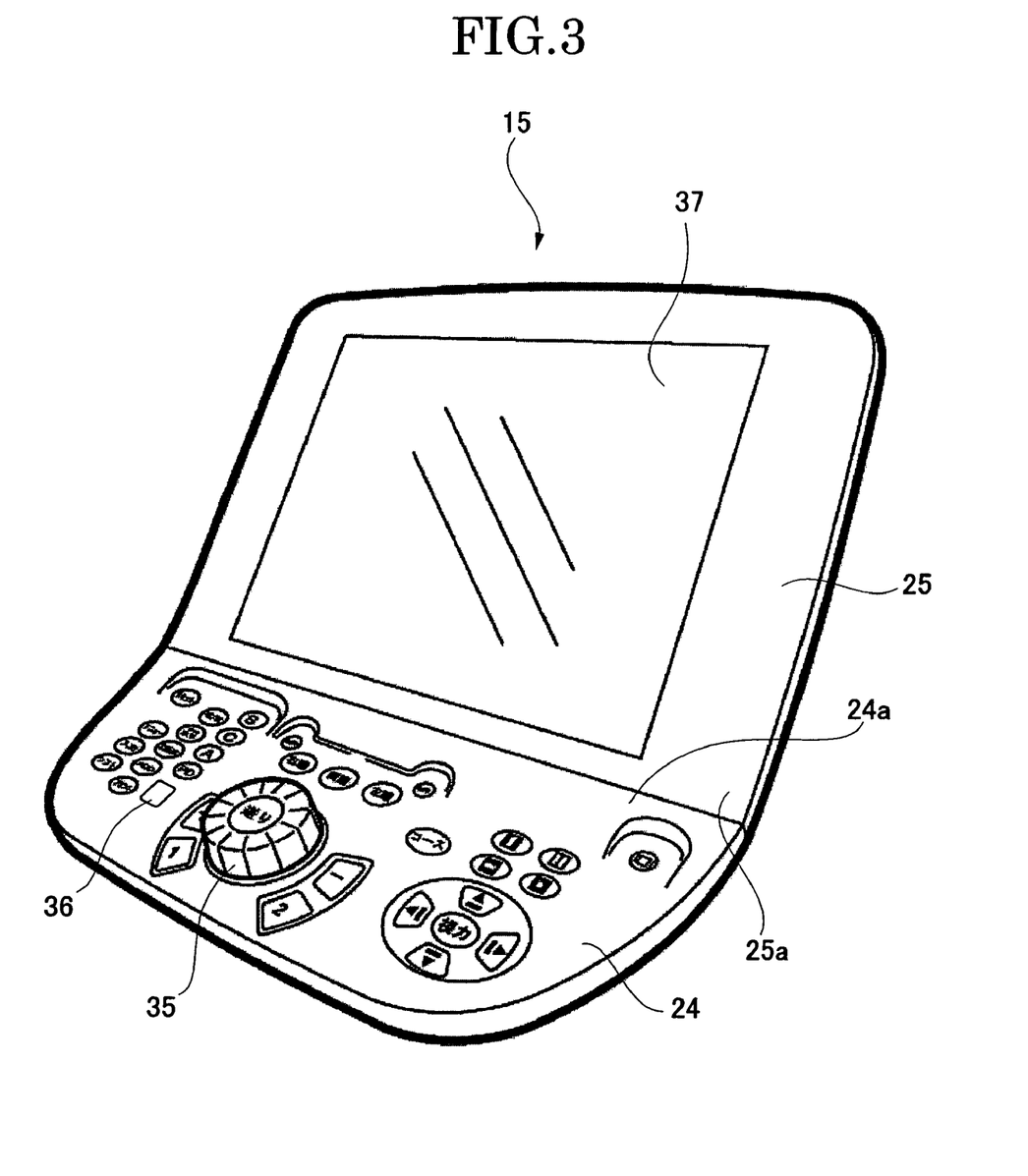
FIG. 3 is a plan view illustrating a controller according to one embodiment of the present invention.

The controller 15 is placed on the optometry table 18. Referring to FIGS. 2, 3, the controller 15 includes an operation section 24 to be operated by an examiner 23 (refer to FIG. 1), a display section 25 for displaying an after-mentioned operation image of the operation section 24, an arithmetic control circuit 26, and an image output section 27.

As illustrated in FIG. 2, the arithmetic control circuit 26 includes a CPU 28 and a memory 29. The CPU 28 is connected to the operation section 24 and the image output section 27, and also to a driving control section (not shown) provided in the corrective device 14. The memory 29 stores target data 30 illustrating the various targets 11 for use in various examinations, operation image data 31 illustrating the above-mentioned operation image, examination data 32 indicating the names and the contents of the various examinations, various calculation programs 33 for use in the calculation by the CPU 28, and refractive power data 34 indicating refractive power such as spheric diopter power, astigmatic diopter power and axial angle of each corrective lens.

The operation section 24 has various switches for use in the setting of the examinations, such as a dial 35 and a display switching switch 36 as illustrated in FIG. 3. The dial 35 is a switch for selecting the corrective lens to be disposed in the optometry window 22 of each of the phoroptors 21. The display switching switch 36 is a switch for switching between an operation image mode that an operation image is displayed on the display section 25 and a target mode that the target 11 is displayed on the display section 25 as described below.

If the dial 35 is operated, the CPU 28 extracts the refractive power corresponding to the operated position of the dial 35 from the refractive power data 34 of the memory 29, and sends to the driving control section of the corrective device 14 the control signal for disposing the corrective lens having the refractive power indicated by the extracted refractive power data in the optometry window 22 of the phoroptor 21. The corrective lens having the refractive power selected by the operation of the dial 35 is thereby disposed in the optometry window 22 of each of the phoroptors 21.

Moreover, if the dial 35 is operated, the CPU 28 sends the signal indicating the refractive power data 34 extracted from the memory 29 to the image output section 27.

Furthermore, for example, if the power source of the visual acuity testing apparatus 10 is switched from the OFF state to the ON state, the CPU 28 reads the operation image data 31 from the memory 29, and sends the signal indicating the operation image data to the image output section 27.

The display section 25 is connected to the image output section 27 as illustrated in FIG. 2. Moreover, the display section 25 includes a display screen 37 onto which the operation image illustrating the contents set by the operation of each of the switches of the operation section 24 is displayed. Furthermore, the display section 25 has a lower end portion 25a rotatably supported about an axial member via the axial member (not shown) provided along an end portion 24a of the operation section 24 as in the example illustrated in FIG. 3.

Figure 4:
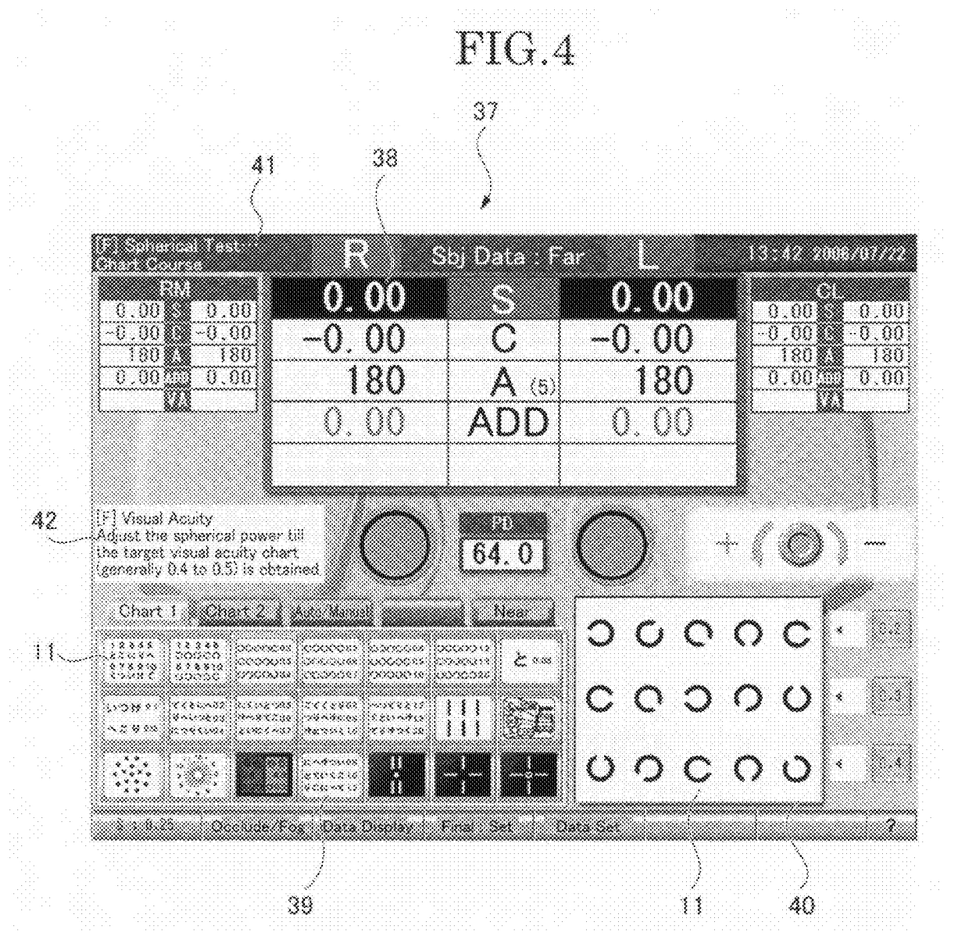
FIG. 4 is a front view illustrating a display screen of a display section according to one embodiment of the present invention.

In the example illustrated in the figures, the display screen 37 is constituted of a liquid crystal panel. As illustrated in FIG. 4, the display screen 37 includes a refractive power display section 38, a list display section 39, and a target display section 40. The refractive power display section 38 displays the refractive power of the corrective lens set by the operation of the dial 35 of the operation section 24. The list display section 39 displays the list of targets 11 to be displayed on the display screen 16 of the target presenting unit 13. The target display section 40 displays the target 11 selected from the list display section 39 for use in the examination. The display screen 37 also includes an examination name display section 41 and an examination contents display section 42. The examination name display section 41 displays the type of the examination which is in progress by the target 11 displayed on the target display section 40. The examination content display section 42 displays the contents of the examination which is in progress.

The refractive power display section 38, the list display section 39, the target display section 40, the examination name display section 41 and the examination content display section 42 are contained in the operation image data 31 stored in the memory 29.

In the present embodiment, a touch panel (not shown) is provided on the display screen 37. The touch panel is disposed on the list display section 39. As is conventionally known, the touch panel includes a pair of panel members such as transparent films and glasses that resistance films are provided in both the end portions thereof and a plurality of conductive film strips are formed in parallel to each other. The touch panel is formed by attaching the pair of panel members such that each of the conductive film strips becomes orthogonal to each other. When the surface of the touch panel is pressed, each of the conductive film strips formed on each of the panel members electrically conducts by having contact to each other. In this case, according to the voltage generated in each of the resistance films, it is detected by the touch sensor that any one of the conductive film strips of one panel member has contact with any one of the conductive film strips of the other panel members. The pressed position of the touch panel is thereby specified. Accordingly, by pressing from the display screen 37, for example, the image illustrating the target 11 for use in the examination in the targets 11 of the list display section 39 displayed on the display screen 37, the target 11 can be selected from the list display section 39. If the touch sensor detects the pressed position, the touch sensor sends the detection signal illustrating the position to the CPU 28.

If the CPU 28 receives the detection signal from the touch sensor, the CPU 28 extracts from the memory 29 the target data 30 corresponding to the target 11 of the pressed position indicated by the detection signal, and sends the signal illustrating the extracted target data 30 to the image output section 27.

Moreover, if the CPU 28 receives the detection signal from the touch sensor, the CPU 28 extracts from the memory 29 the examination data 32 illustrating the examination to be conducted by using the target 11 of the pressed position indicated by the detection signal, and sends the signal illustrating the extracted examination data 32 to the image output section 27.

In the example illustrated in FIG. 2, the image output section 27 includes a first output port 43 for outputting the operation image signal indicating the operation image data 31 received from the CPU 28 and a second output port 44 for outputting the target image signal indicating the target data 30 received from the CPU 28. The image output section 27 also includes a third output port 45 for outputting the refractive power image signal indicating the refractive power data 34 received from the CPU 28 and a fourth output port 46 for outputting the examination image signal indicating the examination data 32 received from the CPU 28.

In the example illustrated in FIG. 2, the first output port 43, the third output port 45 and the fourth output port 46 are connected to the display section 25. The second output port 44 is connected to the display section 25 and the target presenting unit 13.

If the image output section 27 receives the signal indicating the operation image data 31 from the CPU 28, the image output section 27 outputs to the display section 25 via the first output port 43 the operation image signal for displaying the operation image on the display screen 37. The refractive power display section 38, the list display section 39, the target display section 40, the examination name display section 41 and the examination content display section 42 included in the operation image data 31 are thereby displayed on the display screen 37 of the display section 25 as illustrated in FIG. 4.

Moreover, if the image output section 27 receives the signal indicating the refractive power data 34 from the CPU 28, the image output section 27 outputs to the display section 25 via the third output port 45 the refractive power image signal for displaying the refractive power shown by the refractive power data 34 on the refractive power display section 38 included in the operation image data 31. The value of the refractive power of the corrective lens selected by the operation of the dial 35 is thereby displayed on the refractive power display section 38 of the display screen 37 of the display section 25 as illustrated in FIG. 4.

Furthermore, if the image output section 27 receives the signal indicating the examination data 32 from the CPU 28, the image output section 27 outputs to the display section 25 via the fourth output port 46 the examination image signal for displaying the examination name and the examination contents shown by the examination data 32 on the examination name display section 41 and the examination content display section 42, respectively, included in the operation image data 31. The examination name and the examination contents are thereby displayed on the examination name display section 41 and the examination content display section 42 of the display screen 37 of the display section 25, respectively, as illustrated in FIG. 4.

In addition, if the image output section 27 receives the signal indicating the target data 30 from the CPU 28, the image output section 27 outputs to the display section 25 via the second output port 44 the target image signal for displaying the target 11 shown by the target data on the target display section 40. The target 11 selected in the display section 25 is thereby displayed on the target display section 40 of the display section 25 as illustrated in FIG. 4.

Furthermore, if the image output section 27 receives the signal showing the target data 30 from the CPU 28, the image output section 27 outputs to the target presenting unit 13 via the second output port 44 the target image signal for displaying the target 11 shown by the target data on the display screen 16. The target 11 selected in the display section 25 is thereby displayed on the display screen 16 of the target presenting unit 13 as illustrated in FIG. 4.

When examining the visual performance of the subject's eye in a state looking from a distance, if the display section 25 is in the target mode, at first, the examiner 23 switches the display section 25 to the operation image mode by operating the display switching switch 36 provided in the operation section 24. In this case, if the CPU 28 detects that the display switching switch 36 is operated for switching the display section 25 to the operation image mode, the CPU 28 sends to the image output section 27 the control signal for displaying the operation image on the display screen 37 of the display section 25 as described above. The image output section 27 thereby outputs the operation image signal to the display section 25 via the first output port 43, and the operation image is displayed on the display section 25.

Next, the examiner 23 selects the target 11 for use in the examination by the operation of the list display section 39 of the display section 25. In this case, as described above, the selected target 11 is displayed on the target display section 40 of the display section 25. Moreover, the examination name and the contents corresponding to the selected target 11 are displayed on the examination name display section 41 and the examination content display section 42 of the display section 25, respectively. Furthermore, the selected target 11 is displayed on the display screen 16 of the target presenting unit 13. The examiner 23 looks at the target 11 displayed on the target display section 40, the examination name and the contents displayed on the examination name display section 41 and the examination content display section 42, respectively, such that the examiner 23 can confirm whether or not the displayed target 11 matches the selected target 11 and whether or not the examination is conducted by using an appropriate target 11.

Next, the examiner 23 asks the subject 12 to look at the target 11 displayed on the display screen 16 of the target presenting unit 13 via each of the corrective lenses disposed in each of the optometry windows 22, and asks the subject 12 about the viewed level. The examiner 23 switches the corrective lens disposed in each of the optometry windows 22 by the operation of the dial 35 of the operation section 24 according to the response from the subject 12. In this case, the refractive power of the corrective lens set by the operation of the dial 35 is displayed on the refractive power display section 38 of the display section 25 as described above. By switching the corrective lens, the visual performance of the subject's eye is corrected and the refractivity of the eyeglass lens to be made can be defined.

On the other hand, when examining the visual performance of the subject's eye in a state looking at a near side, the examiner 23, at first, disposes the controller 15 in front of the subject 12 on the optometry table 18. In addition, the examiner 23 rotates the display section 25 about the axial member, such that the display screen 37 faces the phoroptors 21.

Next, the examiner 23 switches the display section 25 from the operation image mode to the target mode by the operation of the display switching switch 36. The examiner 23 selects the target 11 for use in the near examination by the operation of the list display section 39 of the display section 25. In this case, if the CPU detects that the display switching switch 36 is operated for switching the display section 25 to the target mode and the target 11 is selected from the list display section 39, the CPU 28 extracts the target data 30 corresponding to the selected target 11 from the memory 29 and sends to the image output section 27 the control signal for conducting the image processing for adjusting the size of the target 11 so as to be a size substantially identical to the size of the display screen 37 without conducting the above processing for displaying the target 11 illustrated by the target data 30 on the target display section 40 of the operation image. Therefore, the image output section 27 conducts the process for adjusting the size of the target 11 according to the control signal from the CPU 28 and outputs to the display section 25 via the second output port 44 the target image signal indicating the target 11 having the adjusted size. The selected target 11 is thereby displayed on the entire display screen 37 of the display section 25.

In this case, by the method proposed in the previous application (JP2006-219492A) of the present inventor, the target 11 can be displayed on the display screen 37 at a size corresponding to the value of the visual power of an examination target and the distance between the display screen 37 and the phoroptor 21. More particularly, the distance between each of the phoroptors 21 and the display screen 37 is calculated by using the calculation program 33 of the memory 29, and the size of the target 11 is adjusted to a size corresponding to the value of visual power of the examination target according to the calculated distance. After that, the target 11 having the adjusted size is displayed on the display screen 37.

Next, the examiner 23 asks the subject 12 to look at the target 11 displayed on the display screen 37 of the display section 25 via each of the corrective lenses disposed in each of the optometry windows 22, and asks the subject 12 about the vision level. After that, similar to the distance examination, the examiner 23 switches the corrective lens disposed in each of the optometry windows 22 according to the response of the subject 12 by means of the operation of the dial 35 of the operation section 24.

When the examiner 23 confirms the operation image in the near examination, the operation image can be displayed on the display screen 37 of the display section 25 by switching the display section 25 to the operation image mode by means of the operation of the display switching switch 36.

When conducting a heterophoria examination for measuring the heterophoric condition of the subject's eye by using the visual acuity testing apparatus 10 according to the embodiment of the present invention, the heterophoria examination can be conventionally performed by attaching a polarizer (not shown) onto the display screen 16 of the target presenting unit 13 or the display screen 37 of the display section 25 and by using the backlight of the target presenting unit 13 or the display section 25. Instated of this, a conventionally known red and green target (not shown) can be displayed on the display screen 16 of the target presenting section 13 or the display screen 37 of the display section 25. In this case, a red and green filter (not shown) is disposed in the optometry window 22 of each of the phoroptors 21, so as to present an individual image to each of the subject's eyes. Thereby, the heterophoria examination can be performed. In addition, instead of these methods, a liquid crystal filter (not shown) can be disposed in the corrective lens disposed in the lens disk in each of the phoroptors 21, for example. In this case, the target 11 for the left eye and the target 11 for the right eye are alternated at a high speed, so as to be displayed on the display screen 16 of the target presenting unit 13 or the display screen 37 of the display section 25, and each of the lens disks is rotated according to the alternate of each target 11. The corrective lens having the liquid crystal filter and the corrective lens without having the liquid crystal filter are thereby alternately disposed in the optometry window 22 of each of the phoroptors 21. Therefore, the heterophoria examination can be conducted by presenting an individual image to each of the subject's eyes.

According to the present embodiment, as described above, the image output section 27 outputs the operation image signal indicating the operation image corresponding to the operation image data 31 extracted from the memory 29 by the CPU 28 to the display section 25 from the first output port 43, and outputs the target image signal indicating the target 11 corresponding to the target data 30 extracted by the CPU 28 to the display section 25 and the target presenting unit 13 from the second output port 44. For this reason, by outputting the target image signal to the target presenting unit 13 from the image output section 27 via the second output port 44, the target 11 selected by the operation of the touch panel provided in the display section 25 can be displayed on the target presenting unit 13.

More particularly, the target presenting unit 13 is constituted of a liquid crystal panel onto which the image shown by the image signals according to the image signals received from the CPU 28 is electrically displayed, and is not constituted of a conventional target presenting unit which extracts target data from a memory section according to a driving control signal from an arithmetic control section and mechanically drives an arrangement device for selectively disposing a target plate corresponding to the extracted target data in front of a subject's eye.

For this reason, according to the embodiment of the present invention, since the memory and the target plates provided in the target presenting unit are not necessary, it is only necessary to add, for example, the new target data 30 into the memory 29 or to change the existing target data 30 stored in the memory 29 to another target data 30 when incorporating the new target 11 into the visual acuity testing apparatus 10. Along the adding and the changing to the memory 29, the adding operation and the changing operation to a member except the memory 29 become unnecessary.

Accordingly, compared with the case that the types of the target 11 presentable in the target presenting unit 13 are required to match the types of the target 11 selectable by the operation of the touch panel provided in the display section 25 as is conventionally done, the new target 11 can be securely and easily incorporated into the visual acuity testing apparatus 10.

Moreover, as described above, the image output section 27 outputs the target image signal to the display section 25 via the second outputting port 44, and the selected target 11 is displayed on the display section 25 together with the operation image and also is displayed so as to be switchable with the operation image. For this reason, the selected target 11 can be easily viewed while looking at the operation image or by switching the display of the display section 25. Accordingly, when the target image signals are output to the display section 25 and the target presenting unit 13, respectively, via the second output port 44 from the image output section 27, for example, the examiner 23 can easily confirm whether or not the target 11 displayed on the target presenting unit 13, i.e., the target 11 presented to the subject 12 conforms to the selected target 11 by looking at the target 11 displayed on the display section 25. Therefore, compared with the case in which the examiner looks into the target presenting unit 13, for example, so as to confirm whether or not the target 11 presented to the subject 12 conforms to the selected target 11, the examination of the visual performance of the subject's eye can be effectively conducted.

The present embodiment illustrates an example in which the selected target 11 is displayed onto the display screen 37 of the display section 25 by switching the display section 25 from the operation image mode to the target mode by the operation of the display switching switch 36 when examining the visual performance of the subject's eye in a state looking from a near side. Instead of this example, as illustrated in FIG. 5, the display screen 37 of the display section 25 can be constituted of a dual viewer (registered trademark) having liquid crystal capable of viewing images different from each other at least from two directions, triple-view liquid crystal, and the like.

In this case, if the image output section 27 receives the signal indicating the operation image data 31 from the CPU 28, the image output section 27 sends to the display section 25 via the first output port 43 the operation image signal for displaying the operation image onto the display screen 37 as described above. The operation image is thereby displayed on the display screen 37 of the display section 25.

Moreover, if the image output section 27 receives the signal indicating the target data 30 from the CPU 28, the image output section 27 outputs to the display section 25 via the second output port 44 the target image signal for displaying the target 11 illustrated by the target data 30 onto the target display section 40 of the operation image. Furthermore, the image output section 27 conducts the image process for adjusting the size of the target 11 such that the size of the target 11 becomes substantially the same as the size of the display screen 37. After conducting the image process, the image output section 27 outputs to the display section 25 via the second output port 44 the target image signal indicating the target 11 having the adjusted size. The operation image including the target display section 40 onto which the selected target 11 is displayed and the target image illustrating the target 11 having a size for the entire area of the display screen 37 are thereby simultaneously displayed on the display screen 37 of the display section 25.

Figure 5:
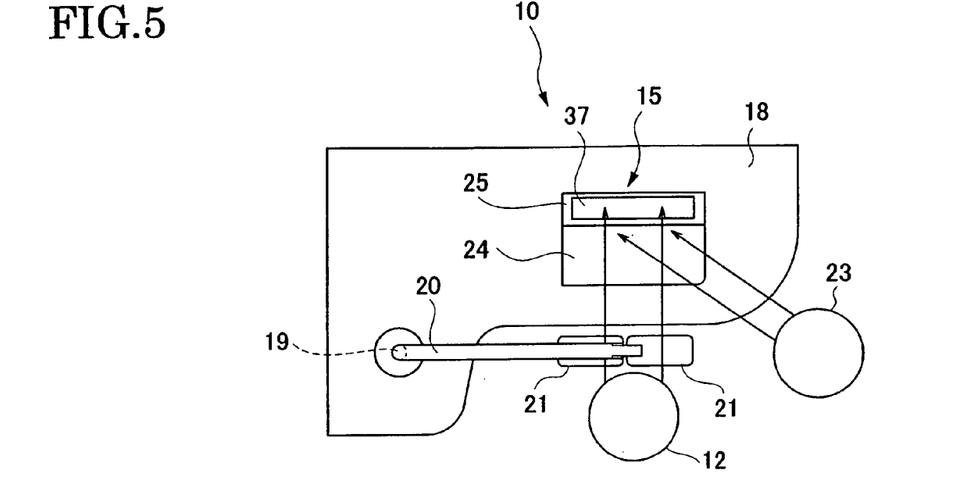
FIG. 5 is an explanatory view illustrating an example in which the display screen of the display section includes dual-view liquid crystal according to one embodiment of the present invention.

In the example illustrated in FIG. 5, the display screen 37 is set such that the target image can be viewed when looking at the display screen 37 from the front face and the operation image can be viewed when looking at the display screen 37 from the right side toward the display screen 37. For this reason, when presenting the target 11 displayed onto the display screen 37 to the subject 12, the distance from the left eye of the subject 12 to the display screen 37 becomes equal to the distance from the right eye of the subject 12 to the display screen 37. The visual performance of the subject's eye can be thereby appropriately examined, compared with the case in which the subject 12 looks at the image displayed onto the display screen 37 from the oblique direction.

According to the example illustrated in FIG. 5, the target image is displayed on the display screen 37 of the display section 25, so as to be visible from the front face of the display screen 37 and so as to be visible from the right side of the display screen 37. Accordingly, when it is necessary to view the operation image while examining the subject's eye in a state looking at a near side, the examiner 23 can view the operation image in a state presenting the target 11 to the subject's eye. Therefore, compared with the case in which, for example, the display of the display section 25 is switched from the target mode displaying the target 11 to the operation image mode displaying the operation image for viewing the operation image, the examination time can be effectively reduced.

FIG. 5 illustrates an example in which the display screen 37 of the display section 25 is set such that images that differ from each other can be visible from two directions. However, instead of this example, the display screen 37 can be set such that different images can be viewed from three directions.

In the example illustrated in FIGS. 1-5, the display screen 16 of the target presenting unit 13 can be constituted of the dual view liquid crystal described in the example illustrated in FIG. 5.

Figure 6:
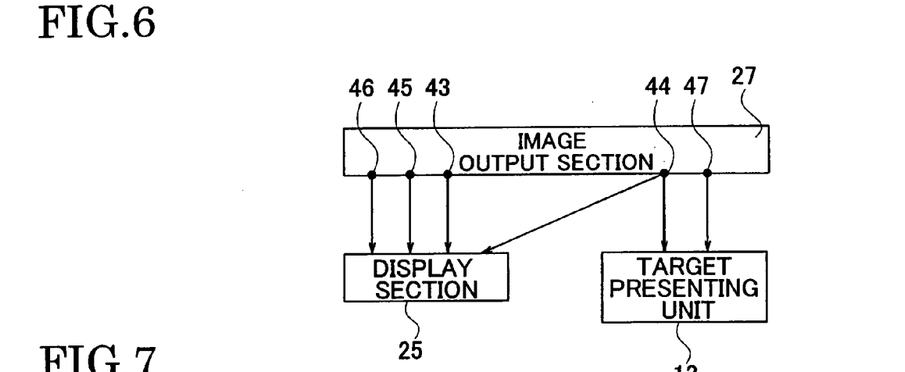
FIG. 6 is a block diagram illustrating an example in which a fifth output port is provided in an image outputting section according to one embodiment of the present invention.

In this case, for example, as illustrated in FIG. 6, advertising data (not shown) illustrating an advertising image is stored in the memory 29, and a fifth output port 47 for outputting an advertising image signal indicating the advertising image to the image output section 27 can be provided. Moreover, when displaying the target 11 onto the target presenting unit 13, the CPU 28 can extract the advertising data from the memory 29 and send the data to the image output section 27, and output the advertising image signal indicating the advertising image to the target presenting unit 13 via the fifth output port 47 from the image output section 27.

In the example illustrated in FIG. 6, the display screen 16 is set such that the target 11 can be visible when looking at the display screen 16 from the front face and the advertising image can be visible when looking at the display screen 16 from the left side, for example. Accordingly, while examining the visual performance of the subject's eye, the advertising image can be presented to a person except the subject 12 such as a person accompanying of the subject 12.

In the examples illustrated in FIGS. 1-6, each of the examples illustrates that the target image signal indicating the target data 30 received from the CPU 28 is output to the display section 25 and the target presenting unit 13 via the second output port 44 from the image output section 27. Instead of these examples or in addition to these examples, as illustrated in FIG. 7, for example, the target image signal can be output to an image display device 48 except the display section 25 and the target presenting unit 13 via the second output port 44 from the image output section 27.

Figure 7:
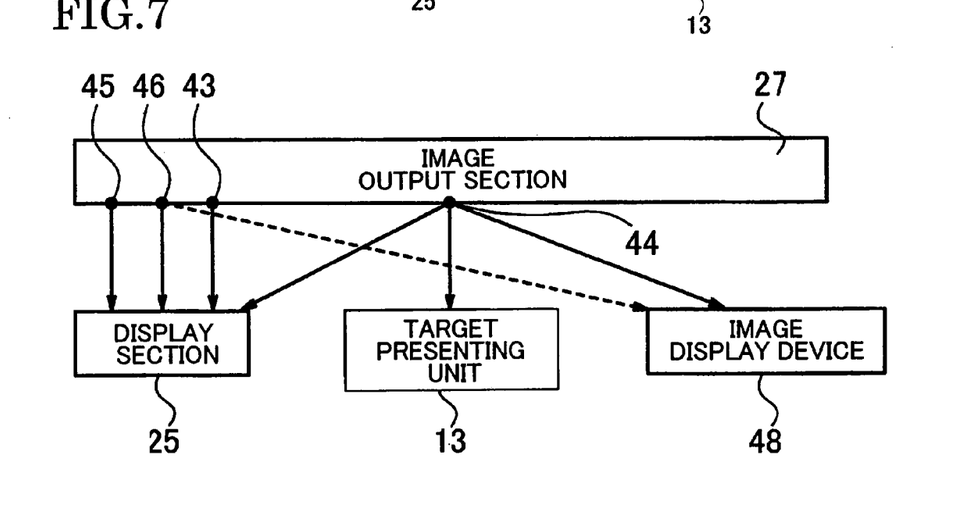
FIG. 7 is a block diagram illustrating an example in which an image signal is output to an image display device except the display section and the target presenting unit from the image output section according to one embodiment of the present invention.

In the example illustrated in FIG. 7, the image display device 48 is constituted of a liquid crystal panel. If the image output section 27 receives the signal indicating the target data 30 from the CPU 28, the image output section 27 outputs the target image signal to the display section 25 and the target presenting unit 13 via the second output port 44 while outputting the target image signal to the image display device 48 as described above. The same target 11 is thereby displayed onto the target display section 40 of the operation image displayed onto the display screen 37 of the display section 25, the display screen 16 of the target presenting unit 13 and the image display device 48.

For example, if the parent comes with the subject 12 such as a child, the parent can understand the visual power of the child based on the examination results and whether or not the child should wear glasses. However, it is difficult for the parent to observe the target 11 presented to the child. For this reason, the size of the character, mark and the like that the child can not see is unknown to the parent. Therefore, the parent may worry about the determination made by the examiner 23 that the child should wear glasses, for example.

On the other hand, according to the example illustrated in FIG. 7, since the image output section 27 outputs the target image signal to the image display device 48 via the second output port 44, the accompanying person can view the target 11 displayed on the image display device 48, i.e., the target 11 presented to the subject 12 by using the image display device 48 for presenting the target 11 to the accompanying person of the subject 12, for example. Accordingly, when the parent comes with the subject 12 such as a child, the parent can easily observe the target 11 presented to the child by viewing the target 11 displayed on the image display device 48. For this reason, the parent can actually recognize the size of the character, mark and the like that the child can not see. Therefore, the parent can be confident in the determination made by the examiner 23 that the child should wear the glasses.

In the example illustrated in FIG. 7, the name of examination which is in progress and the contents of the examination can be displayed onto the image display device 48.

In this case, similar to the above, if the image output section 27 receives a signal indicating the examination data 32 from the CPU 28, the image output section 27 sends to the display section 25 via the fourth output port 46 the examination image signal for displaying the examination name and the examination contents shown by the examination data onto the examination name display section 41 and the examination content display section 42 included in the operation image data 31, respectively, while outputting to the image display device 48 via the fourth output port 46 the examination image signal for displaying the examination name and the examination contents shown by the examination data 32 onto the image display device 48 as illustrated by the dotted line in FIG. 7. In this case, a display area for displaying the image showing the examination name and the examination contents is formed in a position which does not overlap with the target 11, for example, in the image display device 48, and an image showing the examination name and the examination contents is displayed in the display area. The interference of the viewing of the target 11 by the image showing the examination name and the examination contents is thereby prevented.

For this reason, the image showing the name and the contents of the examination which is in progress can be simultaneously displayed on the image display device 48 together with the target 11, in addition to the examination name display section 41 and the examination content display section 42 of the display screen 37 of the display section 25.

Accordingly, when the subject 12 is a child with a parent, by using the image display device 48 for presenting the target 11, the examination name and the examination contents to the parent, the parent can easily confirm the target 11 presented to the child by viewing the display of the image display device 48, and also can understand the name and the contents of the examination which is in progress. Therefore the parent can feel confident in the visual performance examination of the child of the subject 12.

FIGS. 1-7 illustrate an example in which the target display section 40 is provided in the operation image displayed on the display section 25. Instated of this example, an example without having the target displaying section 40 can be used.

In this case, when the display section 25 is switched from the operation image mode to the target mode by the operation of the display switching switch 36, the image output section 27 outputs to the display section 25 via the second output port 44 the target image signal of the target 11 shown by the target data 30 received from the CPU 28 as described above. The target 11 can be thereby displayed on the display screen 37 of the display section 25.

In the examples illustrated in FIGS. 1-7, each of the examples illustrates a case in which the touch panel is provided on the list display section 39 displayed on the display screen 37 of the display section 25 and the target 11 is selected from the list display section 39 by the operation of the touch panel. Instead of these examples or in addition to these examples, a selection switch for selecting various targets is provided in the operation section 24, for example, and the target 11 can be selected by the operation of the selection switch.

Moreover, in FIGS. 1-7, an example in which the display section 25 is rotatably connected to the operation section 24 via the axial member is shown. Instead of this example, the display section 25 can be disposed separately from the operation section 24.

In the examples illustrated in FIGS. 1-7, by connecting the image output section 27, the target presenting unit 13, the display section 25 and the image display device 48 to each other by means of electric wires, the various signals can be output to the target presenting unit 13, the display section 25 and the image display device 48 from the image output section 27 via the electric wires. In the examples illustrated in FIGS. 1-7, the various signals can be output by sending electromagnetic signals to the target presenting unit 13 by means of wireless applications, the display section 25 and the image display device 48 from the image output section 27 without using the electric wires by sending electromagnetic signals.

Although the present invention has been described in terms of exemplary embodiments, it is not limited thereto. It should be appreciated that variations may be made in the embodiments described by a person skilled in the art without departing from the scope of the present invention as defined by the following claims.

What is claimed is:

1. A visual acuity testing apparatus, comprising:
   a target presenting unit for displaying various targets to be presented to a subject's eye;
   an optical element arranging device for retaining various optical elements, and selectively arranging the optical element corresponding to a response from the subject between the subject's eye and the target presenting unit;
   an operation section which is operated for selecting each of targets and each of the optical elements;
   a display section for displaying an operation image illustrating an operation content of the operation section;
   a memory for storing a plurality of target data illustrating each of the targets and operation image data illustrating the operation image;
   an arithmetic control section for extracting the target data and the operation image data from the memory according to an operation of the operation section; and
   an image output section having at least two output ports, wherein
   the image output section outputs to the display section via one output port an operation image signal corresponding to the operation images data extracted by the arithmetic control section, and outputs to at least one of the display section, the target presenting unit and an image display device via the other output port a target image signal corresponding to the target data extracted by the arithmetic control section, and
   wherein the image output section outputs the target image signal to the display section via the other output port, the target selected by the operation of the operation section is displayed on the display section together with the operation image, or the target selected by the operation of the operation section is displayed on the display section to be switchable with the operation image.

2. The visual acuity testing apparatus according to claim 1, wherein the image output section outputs the target image signal to the display section via the other output port, the target selected by the operation of the operation section is displayed on the display section together with the operation image, and the target selected by the operation of the operation section is displayed on the display section to be switchable with the operation image.

3. The visual acuity testing apparatus according to claim 2, wherein the image output section outputs the target image signal to the display device via the other output port.

4. The visual acuity testing apparatus according to claim 3, wherein the memory stores a plurality of examination data illustrating contents of various examinations to be selected by the operation of the operation section, the arithmetic control section extracts the examination data corresponding to the examination selected by the operation of the operation section from the memory, and outputs a signal illustrating the extracted examination data to the image output section, and the image output section outputs to the image display device an examination image signal for displaying onto the image display device an image illustrating the contents of the examination according to a signal from the arithmetic control section.

5. The visual acuity testing apparatus according to claim 1, wherein the image output section outputs the target image signal to the display section via the other output port, the display section includes a liquid crystal panel having liquid crystal capable of viewing images different from each other from at least two directions, the target selected by the operation of the operation section is displayed on the display section to be visible from one direction, and the operation image is displayed on the display section to be visible from the other direction.

6. The visual acuity testing apparatus according to claim 5, wherein the image output section outputs the target image signal to the display device via the other output port.

7. The visual acuity testing apparatus according to clam 6, wherein the memory stores a plurality of examination data illustrating contents of various examinations to be selected by the operation of the operation section, the arithmetic control section extracts the examination data corresponding to the examination selected by the operation of the operation section from the memory, and outputs a signal illustrating the extracted examination data to the image output section, and the image output section outputs to the image display device an examination image signal for displaying onto the image display device an image illustrating the contents of the examination according to a signal the arithmetic control section.

8. The visual acuity testing apparatus according to claim 1, wherein the image output section outputs the target image signal to the image display device via the other output port.

9. The visual acuity testing apparatus according to claim 8, wherein the memory stores a plurality of examination data illustrating contents of various examinations to be selected by the operation of the operation section, the arithmetic control section extracts the examination data corresponding to the examination selected by the operation of the operation section from the memory, and outputs a signal illustrating the extracted examination data to the image output section, and the image output section outputs to the image display device an examination image signal for displaying onto the image display device an image illustrating the contents of the examination according to a signal from the arithmetic control section.

* * * * *